United States Patent
Bailey et al.

(10) Patent No.: US 11,981,297 B2
(45) Date of Patent: May 14, 2024

(54) APPARATUS FOR GENERATION OF AIR-BORNE SPRAY TO REMOVE MALODOR AND CONTAMINATION

(71) Applicant: NUVINAIR, LLC, Plano, TX (US)

(72) Inventors: Kyle Bailey, Plano, TX (US); Jason Bailey, Plano, TX (US)

(73) Assignee: NUVINAIR, LLC, Plano, TX (US)

( * ) Notice: Subject to any disclaimer, the term of this patent is extended or adjusted under 35 U.S.C. 154(b) by 0 days.

(21) Appl. No.: 18/121,944

(22) Filed: Mar. 15, 2023

(65) Prior Publication Data
US 2023/0219534 A1    Jul. 13, 2023

Related U.S. Application Data

(60) Continuation of application No. 17/989,454, filed on Nov. 17, 2022, which is a continuation of application
(Continued)

(51) Int. Cl.
*A61L 9/00* (2006.01)
*A61L 2/22* (2006.01)
(Continued)

(52) U.S. Cl.
CPC ............... *B60S 3/008* (2013.01); *A61L 2/22* (2013.01); *A61L 9/14* (2013.01); *B08B 3/02* (2013.01);
(Continued)

(58) Field of Classification Search
CPC ......... B05B 17/00; B60H 3/0007; A61L 9/01; A61L 2/22; A61L 9/00; B05C 9/00; B01F 3/02
(Continued)

(56) References Cited

U.S. PATENT DOCUMENTS

| 3,420,509 A | 1/1969 | Katzman et al. |
| D262,821 S | 1/1982 | Poore |

(Continued)

FOREIGN PATENT DOCUMENTS

| CN | 1582661 A | 2/2005 |
| CN | 101495190 A | 7/2009 |

(Continued)

OTHER PUBLICATIONS

"CLo2 Efficiency System Demo 8 2015" YouTube Aug. 19, 2015 by ACES Environmental Svcs, LLC.
(Continued)

*Primary Examiner* — Monzer R Chorbaji
(74) *Attorney, Agent, or Firm* — Stephen Y. Liu; Carstens, Allen & Gourley, LLP

(57) ABSTRACT

There is provided a system and method of cleaning surfaces of an enclosable environment of a contamination comprising a microbial and viral load. The method includes the steps of sealing the enclosable environment and placing water, and a solid or gel pack, into a container and generating a vortex the container by rotating an impeller. The agitation causes the solid or gel pack to release a gaseous cleaning agent. An air-borne spray exiting from the container spreads throughout the enclosable environment to contact the surfaces to be cleaned within the enclosable environment. The enclosable environment is maintained closed for an effective time period while the air-borne spray dwells on the surfaces to eliminate or substantially reduce the load of the contamination.

17 Claims, 7 Drawing Sheets

Related U.S. Application Data

No. 16/835,851, filed on Mar. 31, 2020, now Pat. No. 11,535,205, which is a continuation-in-part of application No. 15/895,510, filed on Feb. 13, 2018, now Pat. No. 11,420,599, which is a continuation of application No. 15/253,315, filed on Aug. 31, 2016, now Pat. No. 9,925,959, which is a division of application No. 15/063,931, filed on Mar. 8, 2016, now Pat. No. 9,446,742.

(60) Provisional application No. 62/253,188, filed on Nov. 10, 2015.

(51) Int. Cl.
| | |
|---|---|
| A61L 9/14 | (2006.01) |
| B08B 3/02 | (2006.01) |
| B08B 3/04 | (2006.01) |
| B08B 9/00 | (2006.01) |
| B60S 3/00 | (2006.01) |

(52) U.S. Cl.
CPC ............... B08B 3/04 (2013.01); B08B 9/00 (2013.01); *A61L 2202/16* (2013.01); *A61L 2202/17* (2013.01)

(58) Field of Classification Search
USPC .............. 422/1, 5, 28, 32, 37, 122, 305–306
See application file for complete search history.

(56) References Cited

U.S. PATENT DOCUMENTS

| | | | |
|---|---|---|---|
| 4,482,365 A | 11/1984 | Roach | |
| 5,549,854 A | 8/1996 | Hulthom et al. | |
| 6,273,402 B1 | 8/2001 | Cheng | |
| 6,764,661 B1 | 7/2004 | Girard | |
| D588,687 S | 3/2009 | Drucker et al. | |
| 7,846,227 B2 | 12/2010 | Gotoh et al. | |
| D635,403 S | 4/2011 | Conway et al. | |
| D648,016 S | 11/2011 | Choi et al. | |
| 8,221,678 B2 | 7/2012 | Hedman | |
| D711,523 S | 8/2014 | Hsiao | |
| D711,524 S | 8/2014 | Hsiao | |
| 9,433,695 B2 | 9/2016 | Aamodt et al. | |
| 9,446,742 B1 | 9/2016 | Bailey et al. | |
| D795,407 S | 8/2017 | Skoda et al. | |
| 9,925,959 B2 | 3/2018 | Bailey et al. | |
| D952,824 S | 5/2022 | Yang | |
| D997,327 S | 8/2023 | Xing et al. | |
| 2004/0009094 A1 | 1/2004 | Adiga et al. | |
| 2005/0031486 A1 | 2/2005 | Mole et al. | |
| 2005/0074359 A1 | 4/2005 | Krieger et al. | |
| 2006/0067854 A1 | 3/2006 | Andino et al. | |
| 2008/0283626 A1 | 11/2008 | Aldana et al. | |
| 2008/0292507 A1 | 11/2008 | Dee et al. | |
| 2009/0148342 A1 | 6/2009 | Bromberg et al. | |
| 2012/0174792 A1* | 7/2012 | Chang | A61L 9/22 96/52 |
| 2013/0028787 A1 | 1/2013 | Takeuchi et al. | |
| 2013/0079733 A1* | 3/2013 | Burt | B05B 17/0607 239/102.1 |
| 2013/0136685 A1 | 5/2013 | Baselli et al. | |
| 2013/0189153 A1 | 7/2013 | Carson et al. | |
| 2014/0115765 A1 | 5/2014 | Carpenter et al. | |
| 2014/0271355 A1 | 9/2014 | Mason | |

FOREIGN PATENT DOCUMENTS

| | | |
|---|---|---|
| CN | 101537203 A | 9/2009 |
| CN | 104321137 A | 1/2015 |
| JP | 2003040712 A | 2/2003 |
| JP | 2009051018 A | 3/2009 |
| JP | 2009234887 A | 10/2009 |
| KR | 101457648 B1 | 10/2014 |
| WO | 2006076033 A1 | 7/2006 |
| WO | 2009114962 A1 | 9/2009 |
| WO | 2015100866 A1 | 7/2015 |
| WO | 2017091354 A2 | 6/2017 |

OTHER PUBLICATIONS

"How to Use a Biocide Systems Car Deoderizer" YouTube Jun. 16, 2014 by StreetsideAuto.com.
"Odor Removal & Ozone Generator Usage" YouTube Mar. 12, 2009 by Detail King.
Air Clenz Ordor Eliminating Tablet, www.airclenz.com, Feb. 6, 2014, 11 pages.
Biocide Systems, "Auto Shocker Quick Release Care Odor Eliminator", dated Jul. 30, 2013, https://web.archive.org/web/20130730134349/http://www.biocidesystems.com:80/autoshocker1.html, accessed on Dec. 9, 2023, 3 pages.
Promixx The Original Vortex Mixer & Best Protein Shaker, "Introducing the World's Most Advanced Sports Bottle!", dated Oct. 29, 2014, https://web.archive.org/web/20141029052233/http://www.promixx.com/, accessed Dec. 5, 2023, 7 pages.

\* cited by examiner
APPARATUS FOR GENERATION OF AIR-BORNE SPRAY TO REMOVE MALODOR AND CONTAMINATION

STATEMENT OF RELATED APPLICATIONS

This application is a continuation of U.S. Ser. No. 17/989,454, filed on Nov. 17, 2022, which is a continuation of U.S. Ser. No. 16/835,851, filed on Mar. 31, 2020, issued as U.S. Pat. No. 11,535,205, which is a continuation-in-part application of U.S. Ser. No. 15/895,510, filed Feb. 13, 2018, issued as U.S. Pat. No. 11,420,599, which is in turn a continuation of application U.S. Ser. No. 15/253,315, filed Aug. 31, 2016, issued as U.S. Pat. No. 9,925,959, which is in turn a divisional application of U.S. Ser. No. 15/063,931, filed on Mar. 8, 2016, and issued as U.S. Pat. No. 9,446,742, which claims the benefit of provisional application 62/253,188, filed on Nov. 10, 2015.

BACKGROUND

1. Field of the Invention

The present technology relates to apparatus and systems for air-borne dispersal of a cleaning agent onto contaminated surfaces to clean these surfaces. More particularly, the technology relates to cleaning of surfaces, contaminated with microbial and/or a viral load that may be hazardous to human health and that may lead to contagion, in enclosed spaces, such as vehicle people-carrying spaces, to reduce or eliminate the contamination.

2. Description of the Related Art

There is increasing concern about the spread of contagious diseases, whether these may be influenza, common colds, or a potentially lethal virus such as Ebola, or microbial or viral diseases that are not even known or identified at this time. For purposes of this description, microscopic fungi are included in the term "microbes." Most of these microbes and viruses are spread through contact; a first person contacts some surface (for example, by shaking the hand of a contagious person or touches a contaminated surface) and acquires the contamination, becomes infected, and then passes it on to yet another person. This chain of infection is well-known. Some contaminants, whether microbial or viral, appear to be spread through air-borne means. This includes coughing and the emitting of a fine spray of contaminated and contagious sputum.

In a modern urban environment, one of the main means of transportation is in enclosed vehicles such as, but not limited to, aircraft, busses, trains, boats, cars, SUVs and trucks. Some of these are vehicles that are open to the general public to use, and some members of the public may have a communicable disease that is spread through microbes or viruses. Surfaces inside the cabin of the vehicle, where passengers are usually seated, may over time become heavily contaminated with live microbes and viral contaminants. Thus, these surfaces serve to spread the microbial or viral disease to other passengers through contact.

Even in non-public, personal or family transportation, one family member may be ill and could contaminate surfaces thereby passing a contagious illness to other family members. This is especially a risk where school-aged children "pick up" a microbial or viral infection from classmates at school, and can then pass it on to parents and siblings through contaminated surfaces in a family vehicle. Some microbes or viruses may be long-lived, and immunity to these may not be readily achieved. Thus, there is a chance of recurrent illness. Merely wiping surfaces may not eliminate the microbial or viral load on surfaces because surfaces may not be smooth and totally accessible. For example, surfaces are often textured and may have joints and other features where microbial and viral loads may persist.

With regard to newly manufactured vehicles, the chances of a microbial or viral load on surfaces are low, unless the vehicle was contaminated during assembly. On the other hand, the chances that a "pre-owned" or "used" vehicle is contaminated and a source of potential infection, is relatively far higher. Aside from the potential health issues, there are often also aesthetic issues with pre-owned or used cars: they may have an odor in the cabin space from pets carried in the space or from the way in which they were (mis)used by the previous owners. This can have a negative impact on the resale value of the vehicle.

There is a need from a public health standpoint to clean surfaces within a passenger carrying cabin space of vehicles to reduce any microbial and/or viral load. Moreover, there is also not only a public health need to do this but also a business or economic need to remove any undesirable odors from the cabin space of public, used or pre-owned vehicles.

SUMMARY

This summary is intended to present a brief outline of some of the features of exemplary embodiments of the inventions; these and additional features are more particularly described in the Detailed Description, here below. The descriptions do not limit the scope on the inventions, which is set forth in the appended patent claims.

In an exemplary embodiment, there is provided a method of cleaning surfaces of an interior cabin space of a contamination comprising a microbial and viral load. The method includes the steps of sealing the interior cabin space and placing water, and a solid or gel pack, into a container of the apparatus. If the lid is closed, the nozzle should preferably be open to avoid pressure build up in the container. The motor of the apparatus is activated to agitate the water and generate a vortex of water within a container of the apparatus by rotating an impeller in the container. The agitation causes the solid or gel pack to release a gaseous cleaning agent. The steps then include opening a nozzle of the lid of the apparatus, if it was not already open, to generate an air-borne spray from the nozzle. The spray includes the gaseous agent, along with very fine entrained mist of water. The lid knocks out at least some of the larger sized droplets of water that might have been entrained in the air-borne spray, prior to exit of the air-borne spray from the nozzle. The air-borne spray exiting from the container spreads throughout the interior cabin space to coat the surfaces to be cleaned within the interior cabin space. The cabin is maintained closed for an effective time period while the coating from the air-borne spray dwells on the surfaces to eliminate or substantially reduce the load of the contamination. The apparatus used in carrying out this method includes a substantially frusto-conical container having a circular first end and a circular second end, wherein the circular second end has a greater diameter than a diameter of the circular first end. The sides of the container are slightly convex near the first end so that the sides of the container are curved. The apparatus includes a housing containing an electric motor and the housing is releasably and sealingly attached to the circular first end of the container. The housing has a base whereon the apparatus can stands upright when assembled and in use. The apparatus includes a spindle with an impeller, driven by the electric motor, located within the container to agitate the water with the solid or the gel pack. The container has a lid sized and configured to releasably and sealingly engage the second end of the container. The lid has a liquid baffle inside, at a distal region of the lid, and the lid has a nozzle extending from the top of the lid that has a cover for sealing the lid and container closed.

Optionally, the step of sealing the interior cabin space comprises closing doors, windows and air vents of an air circulation system of a vehicle cabin.

Optionally, the solid or gel pack includes a formulation that upon contact with water releases chlorine dioxide as the gaseous cleaning agent.

Optionally, the step of sealing the interior cabin space comprises closing doors, windows and air vents of an air circulation system of a vehicle cabin; and may further comprise turning on an air circulation system of the cabin.

Optionally, the step of allowing the cabin to remain closed while the coating from the air-borne spray dwells on the interior of the surfaces to eliminate or substantially reduce the remove or reduce the load of the contamination is for an effective time period of at least 20 minutes.

Optionally, the method further includes using a detector to determine a concentration of the gaseous cleaning agent in the air within the interior cabin space. And the method includes opening the cabin when the concentration is at a safe level.

Optionally, the step of using a detector includes observing an indicator of the apparatus that indicates a safe level of concentration of the gaseous cleaning agent.

Optionally, the motor of the apparatus is powered by a rechargeable battery or by a connection to a power outlet located within the cabin space.

Optionally, the apparatus is sized to fit inside a cup-holder inside the cabin space.

Optionally, the step of activating the motor of the apparatus is carried out remotely.

Optionally, the step of opening a nozzle of the lid is carried out remotely.

Optionally, the step of allowing the cabin to remain closed, while the coating from the air-borne spray dwells on the interior of the surfaces to eliminate or substantially reduce the remove or reduce the load of the contamination, further includes removing odors from the cabin interior.

In another exemplary embodiment, there is provided a system for cleaning a cabin interior of a car, truck, SUV or tractor-trailer rig of a microbial or viral contamination. The system includes sealing the cabin from the outside environment and starting an air recirculation system of the cabin. It also includes selecting a portable apparatus to place inside the cabin interior, where the apparatus includes a substantially frusto-conical container having a circular first end and a circular second end, wherein the circular second end has a greater diameter than a diameter of the circular first end. A housing containing an electric motor is releasably and sealingly attached to the circular first end of the container. And, the housing has a base whereon the apparatus stands upright, when assembled and in use. There is a spindle with an impeller, driven by the electric motor, in the container to agitate the water along with a solid or a gel pack that releases a gaseous cleaning agent. A lid is sized and configured to releasably and sealingly engage the second end of the container, and has a liquid baffle inside at a distal region of the lid. The lid having a nozzle extending from the top of the lid; the nozzle has a cover for sealing the lid and container closed, and the nozzle is sized for projecting an air-borne spray out of it at a velocity that would spread a gaseous cleaning agent throughout the cabin space. The system includes adding a predetermined quantity of water and a chemical that releases a gaseous cleaning agent into the container of the apparatus, and closing the lid of the apparatus, preferably keeping the nozzle open. Then in a further step, the system includes activating the motor of the apparatus to cause formation of a vortex of water in the container through action of the spinning impeller. Entrained larger water droplets are knocked out of the spray exiting out of the nozzle and the nozzle emits an air-borne spray that includes the gaseous cleaning agent, which may include fine water droplets. To allow cleaning to take place, the system maintains the cabin closed while allowing a coating of the emitted gaseous cleaning agent to dwell for an effective time to reduce a microbial and viral load on interior surfaces within the closed cabin.

Optionally, the apparatus is sized to fit inside a cup-holder inside the cabin space and the motor of the apparatus is powered by connection to a power outlet located within the cabin space.

Optionally, the apparatus includes a detector and an indicator to indicate when a concentration of the gaseous cleaning agent has reduced to a safe level.

Optionally, the step of activating the motor of the apparatus is carried out remotely.

Optionally, maintaining the cabin closed also permits the cleaning agent to remove odors from the cabin interior. Optionally, allowing the cleaning agent to dwell for an effective time on the surfaces to be cleaned by keeping the cabin sealed includes maintaining the cabin closed for about 12 to about 30 minutes.

BRIEF DESCRIPTION OF THE DRAWINGS

The foregoing aspects and many of the attendant advantages, of the present technology will become more readily appreciated by reference to the following Detailed Description, when taken in conjunction with the accompanying simplified drawings of exemplary embodiments. The drawings, briefly described here below, are not to scale, are presented for ease of explanation and do not limit the scope of the inventions recited in the accompanying patent claims.

DETAILED DESCRIPTION

In the following non-limiting detailed descriptions of examples of embodiments of the inventions may refer to appended Figure drawings and are not limited to the drawings, which are merely presented for enhancing explanations of features of the technology. In addition, the detailed descriptions may refer to particular terms of art, some of which are defined herein, as appropriate and necessary for clarity.

The term "cabin" as used in the specification and claims refer to a space containing contaminated surfaces that can readily be enclosed, for example by closing doors, windows and air vent system, if any, of the space such that air inside the space is neither withdrawn nor added to. The air may be allowed to re-circulate in the cabin however, by activation of an air circulation system, for example, or use of a fan in the cabin.

The term "coating" or "coat" as is used in reference to a gaseous cleaning agent on surfaces, means that the gaseous agent dwells on the surface and may be carrying entrained fine water droplets that form a mist containing dissolved gaseous cleaning agent so that the air-borne mist coats and thereby cleans the surfaces, including fine surface textures, surface patterns, and tight interstitial spaces such as found, for example, in stitched seats and dash boards, etc. in vehicles.

The terms "contamination" or "contamination load" when used in reference to surfaces within a cabin means microbial, fungal, or viral contamination and also includes contaminants that cause a malodorous scent, for example, of decayed organic matter, fecal matter, and the like.

The term "effective period of time" as it relates to the time that the cleaning agent dwells in a cabin for cleaning of surfaces therein, the effective period may vary from about 10 to about 30 minutes; and in particular may be from about 15 to about 20 minutes. More or less time may also be effective, depending upon the degree of cleaning (extent of contaminant load reduction) to be achieved and the nature of the chemical cleaning agent used. For example, some cabin spaces may have surfaces so heavily contaminated as to require more than one treatment, or to require that the gaseous cleaning agent dwell on surfaces for up to 8 hours, or overnight, to achieve a desired level of cleanliness and deodorization.

The term "significant reduction in contamination load" means that the contamination load of a particular contaminating species is reduced by at least 80% after cleaning in exemplary embodiments, or in some exemplary embodiments at least 98% after cleaning.

Figure 1:
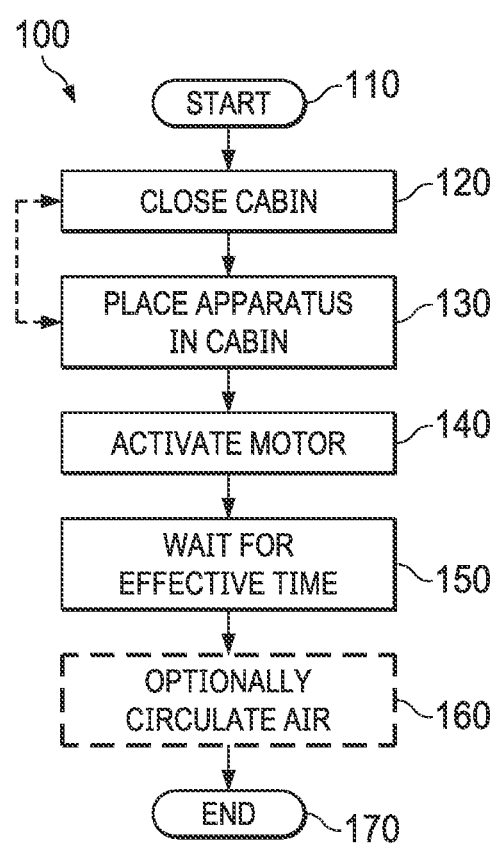
FIG. 1 is a schematic flow diagram of an exemplary embodiment illustrating some of the steps of the method of cleaning contaminated surfaces in an enclosed space.
Figure 2A:
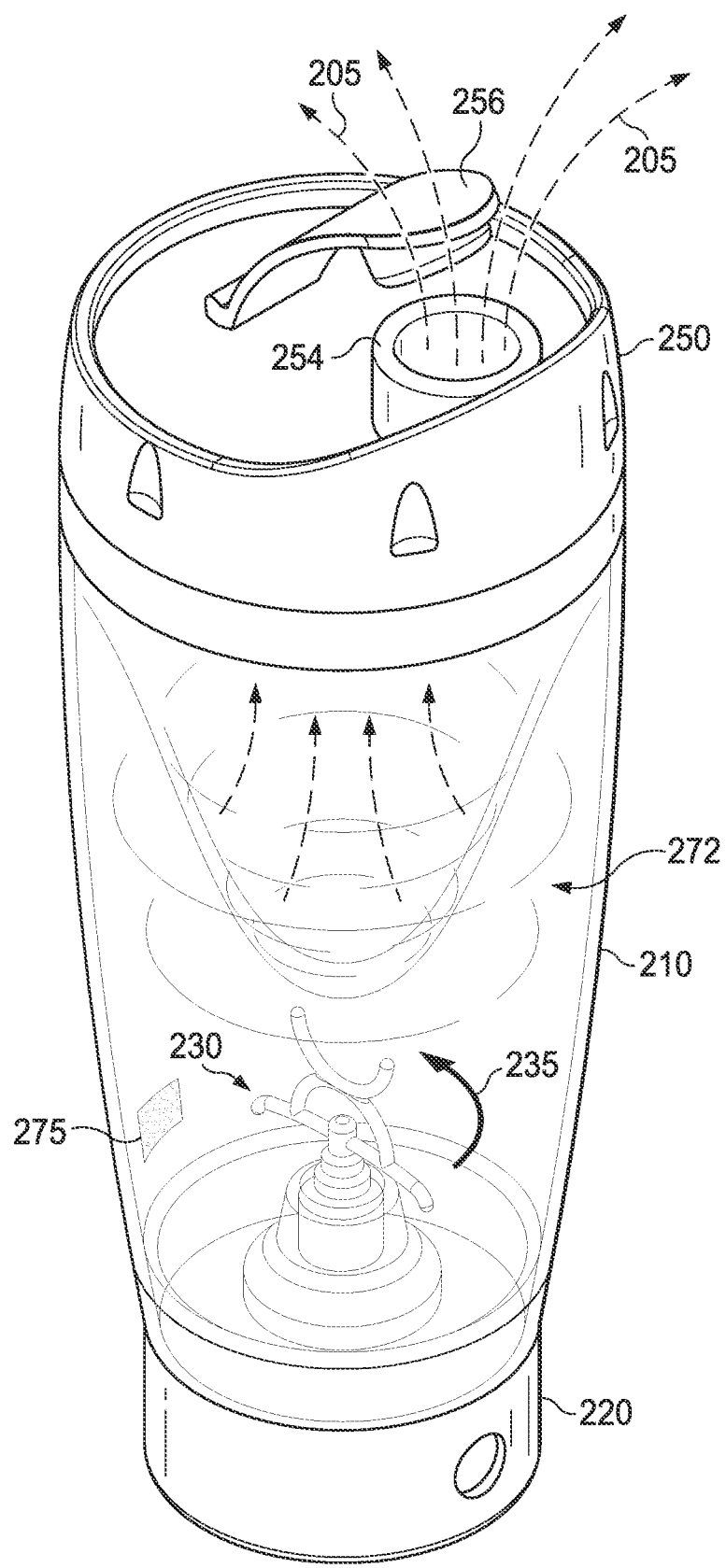
FIG. 2A is an exemplary embodiment of an apparatus showing the generation of a gaseous cleaning agent from its container.
Figure 2B:
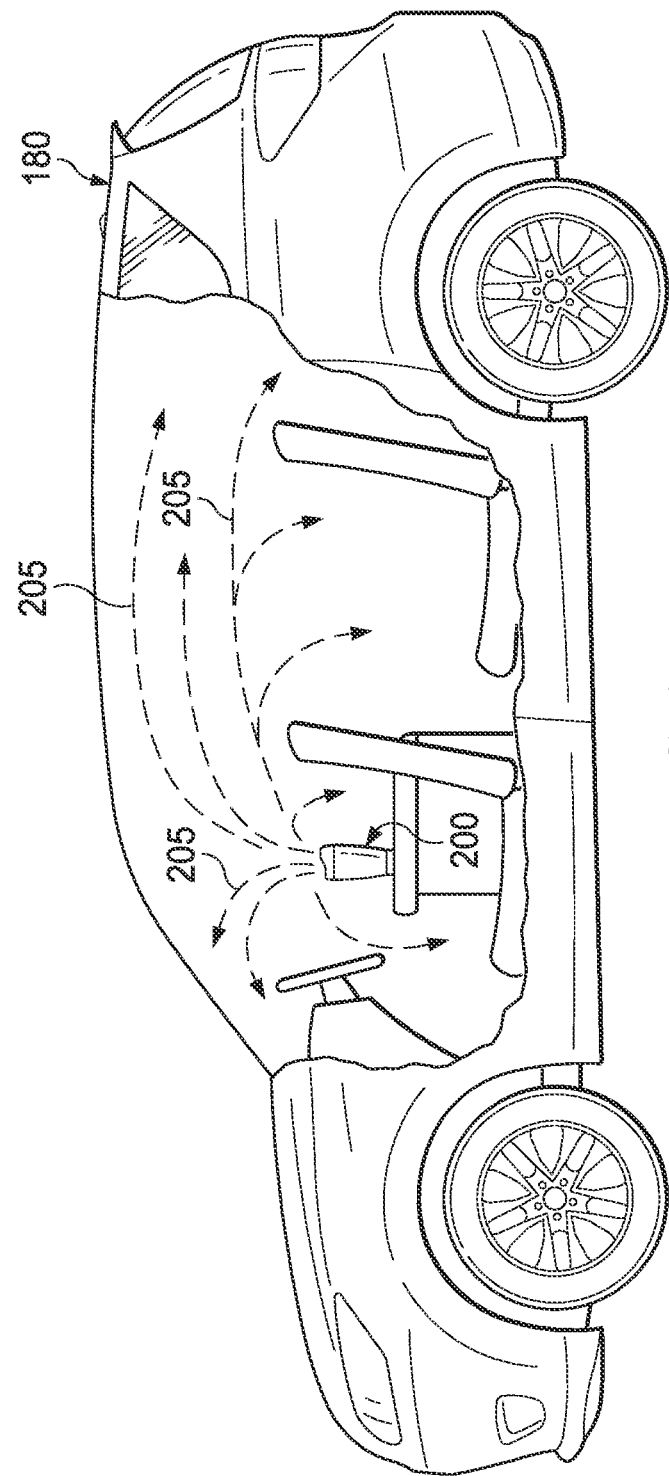
FIG. 2B is an exemplary cutaway illustration of a vehicle showing the exemplary embodiment of the apparatus of FIG. 2A emitting an air-borne gaseous cleaning agent throughout the cabin.
Figure 3A:
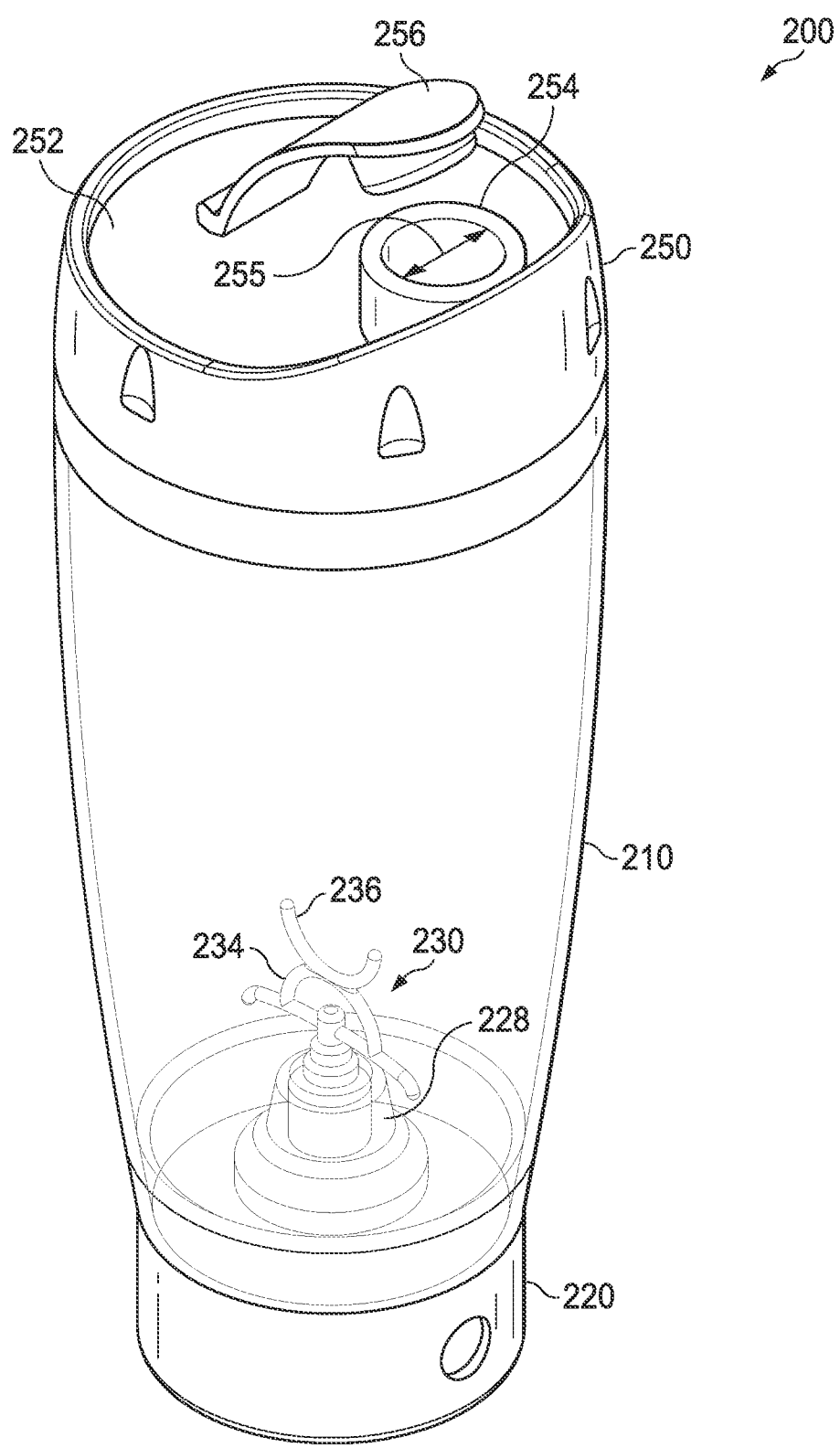
FIG. 3A is a schematic illustration of an exemplary embodiment of an apparatus useful in the methods and systems for cleaning contaminated surfaces in an enclosed space.
Figure 3B:
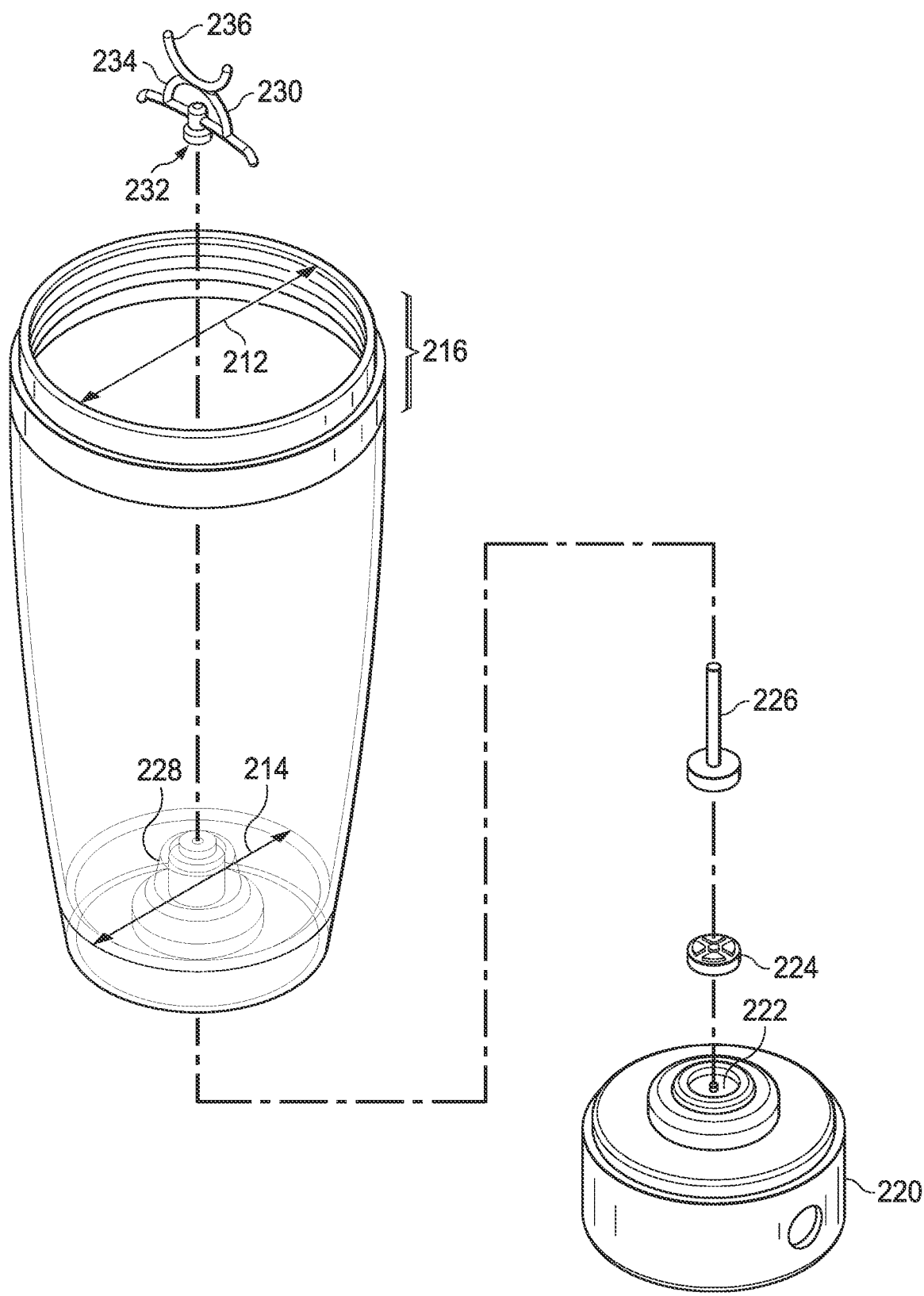
FIG. 3B is an exploded view showing components of the apparatus of FIG. 3A.

Referring to FIG. 1, an exemplary flowchart, there are several straightforward steps in the system or method depicted. Once the process starts at block 110, the cabin with contaminated surfaces inside to be treated is closed at block 120. For example, in a used car such as exemplified in FIG. 2 as 180, all doors, windows and the air circulation system, are closed off. Thus, air does not enter or leave the cabin except for natural flow around seals of doors and windows, which may occur in a closed cabin. A door is opened, and an apparatus (explained later with reference to FIGS. 3A and B, and 4A and B) containing liquid with a chemical in solid or gel pack form is placed in the cabin at block 130, and the cabin is closed. (Note that step 120 may take place after step 130; the order is not important). After a few minutes, the chemical in the closed apparatus generates a gaseous cleaning agent and the water becomes slightly cloudy as a result. At this stage the motor of the apparatus is activated in block 140. A nozzle of the apparatus is open, if it was not open already, and the nozzle is sized such that flow of gaseous agent through the nozzle erupts upward, as lava from a volcano, and flows throughout the cabin interior, as shown in FIG. 2B by arrows 205. The nozzle, as explained below, has internal structures, like baffles, that remove entrained large liquid droplets from the gaseous cleaning agent stream as it exits from the apparatus. It is theorized, without being bound, that smaller fine droplets are entrained and assist in the coating and permeation of surfaces with the gaseous cleaning agent. As with any chemical cleaning agent, the agent should be allowed to dwell on the surfaces for a period of time effective for a significant reduction in the contamination load, as in block 150. Optionally, during this period of waiting (block 150), the vehicle being treated (block 160) may activate the air circulation system, in recirculation mode. this would allow the cleaning agent to enter the ducting and filters that form part of the air circulation system and clean these of potential allergens, microbes, viruses and fungi, as well. After an effective period of time has elapsed, and entry into the cabin is deemed safe, the cabin can be opened in block 170, and the cleaning process is complete.

An exemplary embodiment of an apparatus useful in carrying out the systems and methods of the invention is illustrated in FIGS. 3A, 3B and 4A and 4B. As shown, the apparatus 200 has a container 210, with sides that are gently convex-curved, and that has a base 220 at one end and a lid 250 at the other end. The container 210 has a diameter 212 at its upper end that is larger than its diameter 214 near its base 220. The base 220 contains a motor driven by either a battery pack (rechargeable or not) inside the base, or by electrical connection to an electrical outlet. A spindle 226 is seated on an engaging wheel 224 that engages with motor spindle 222 and rotates in unison with motor spindle 222. An impeller 230 has a cavity 232 that friction fits to the spindle 226 so that the impeller 230 rotates as the spindle 226 rotates. The impeller in the exemplary embodiment shown has a "double horse-shoe shape" with one horse shoe 234 curved downward, and the other 236 curved upward so that the two are conjoined in a common plane at their respective apexes of curvature. This design facilitates creation of a vortex shape when liquid in container 210 is agitated by the rotating impeller in the container at speed. A protective cover 228 shields the motor from contents of the container 210, and fits around the spindle 226, which projects out axially through a hole in the center of the cover. The spindle is appropriately sealed against the hole to avoid or minimize leakage into a space under the cover 228.

Figure 4A:
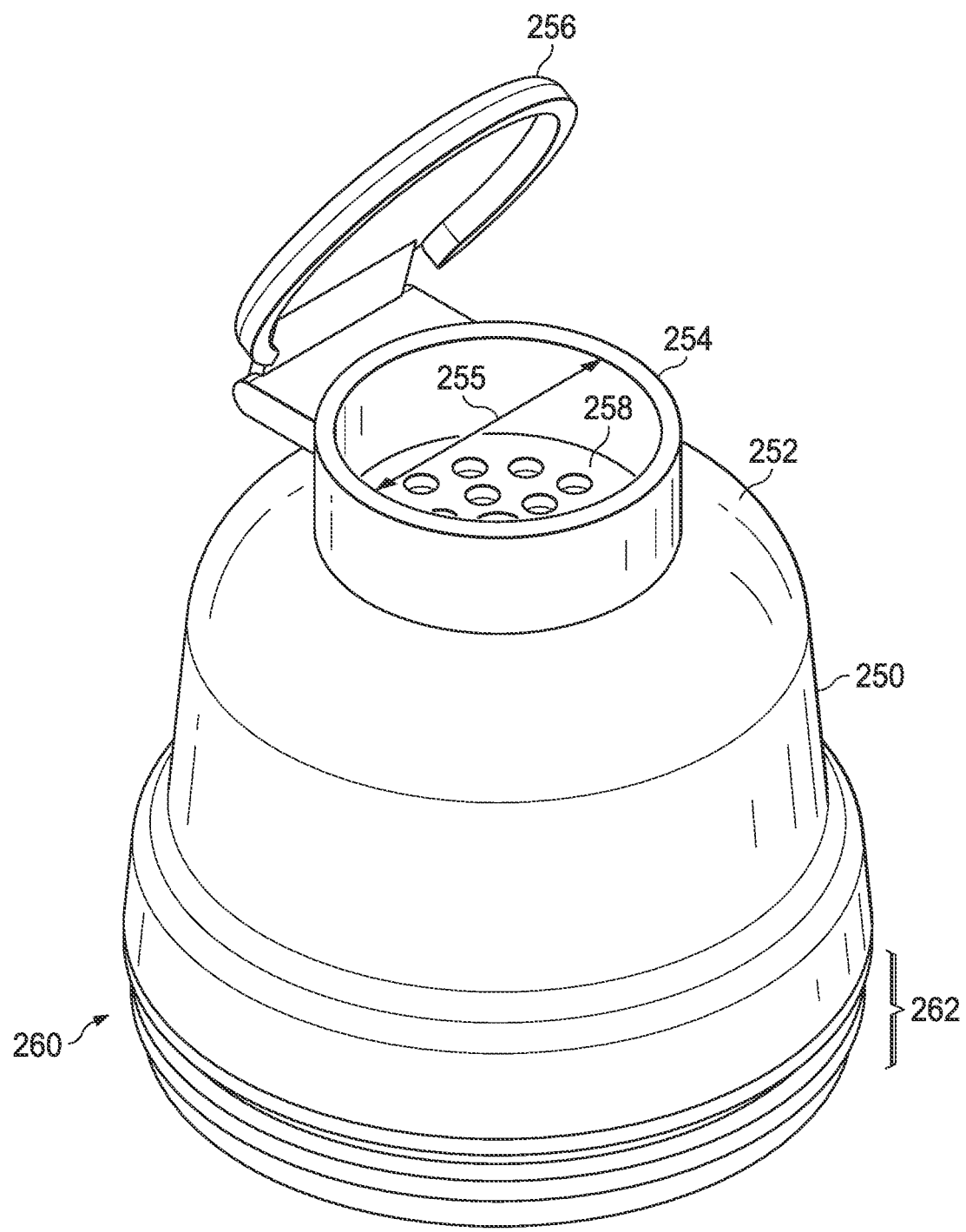
FIGS. 4A and B depict alternative views of another exemplary lid for an exemplary apparatus like that of FIGS. 3A and B.
Figure 4B:
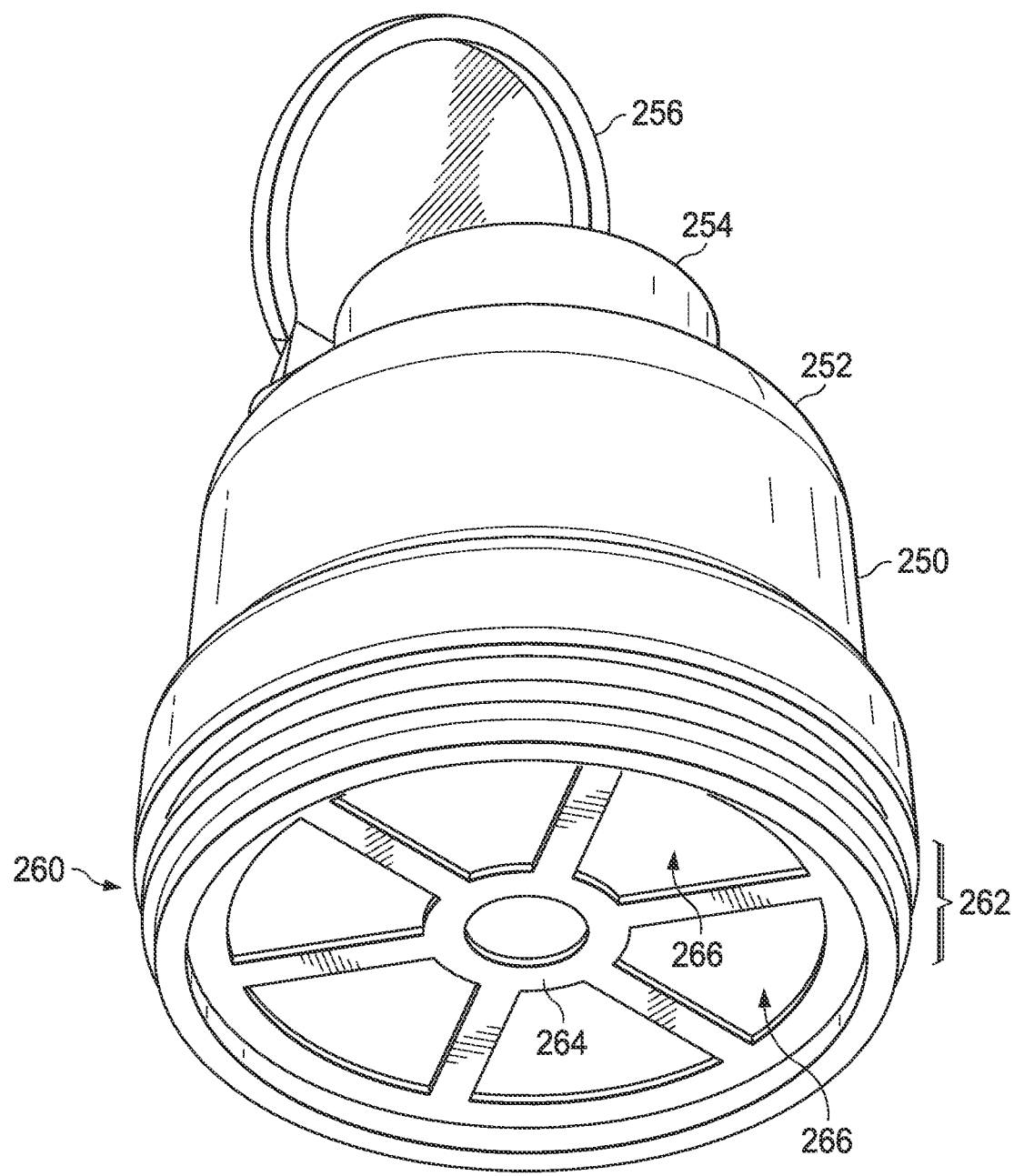

Referring more particularly to FIGS. 4A and B, an alternative illustrated exemplary embodiment of the lid 250 can be either friction fit to the upper end of the container 210 by engaging an upper lip of the container, or can be screwed onto the container 210 by threading 260 on the lower end 262 of lid 250 that engages corresponding threading on the container upper lip (not shown). The lid 250 has a top 252 that has a nozzle 254, equipped with a nozzle closing tab 256, extending from it. Referring briefly to FIG. 2A, when in use, the exemplary container 210 is partially filled with water 272, and a solid 275 or a gel pack 275 that releases the gaseous cleaning agent when in contact with water, is placed in the water container. The cleaning gas begins to evolve more quickly when the motor is activated; gas evolution accelerates due to agitation from rotating impeller 230, as shown by arrow 235, which causes the water to form a vortex in the container 210, as shown. Once sufficient gaseous agent has evolved, the gaseous cleaning agent erupts upward out through the nozzle as an air-borne spray to fill the cabin space and commence cleaning surfaces. Thus, the nozzle 254 has an inner diameter 255 shown in FIG. 4A that is sized to cause gaseous cleaning agent emissions from the container through the nozzle at a speed such that the emissions have both velocity and momentum to cause an air-borne spray that travels throughout the desired region of the cabin space to be cleaned. For example, the air-borne spray velocity is sufficient to travel through the cabin of a car. In other embodiments, such as for a large SUV or a cabin of a tractor trailer rig, more than one apparatus may be needed to achieve total cabin permeation by the air-borne spray. To avoid emitting foam and/or large droplets from the container, the lid includes a baffle 264, exemplified by a cart-wheel structure with spaces between the spokes covered with a fine mesh material 266, in its base area. In addition, the nozzle may include a further baffle 258, at its base, that includes perforations for flow of the gaseous cleaning agent.

While the gaseous cleaning agent has been described as chlorine dioxide, other similar gaseous agents may also be useful. In addition, odorizers may be added to impart a pleasant smell to the interior of the cleaned cabin, or to mask any "chemical" smell.

While examples of embodiments of the technology have been presented and described in text and some examples also by way of illustration, it will be appreciated that various changes and modifications may be made in the described technology without departing from the scope of the inventions, which are set forth in and only limited by the scope of the appended patent claims, as properly interpreted and construed.

What is claimed is:

1. An apparatus for generating and distributing a gaseous cleaning agent, the apparatus comprising:
    a container configured to contain water and a formulation, the formulation producing a gaseous cleaning agent when in contact with water;
    a lid configured to close the container, the lid having a nozzle configured to release the gaseous cleaning agent from the container during use, the lid comprising a baffle configured to selectively allow passage of droplets of water based on droplet size, the baffle having a plurality of perforations;
    an impeller located in the container, the impeller configured to form a vortex within the water in the container, when rotated by the motor during use; and
    a motor coupled to the impeller, the motor contained within a housing disposed at a bottom end of the container;
    wherein the lid and nozzle are configured to emit an air-borne spray comprising gaseous cleaning agent and entrained water through the nozzle.

2. The apparatus of claim 1, wherein the nozzle comprises a baffle, the baffle comprising through holes.

3. The apparatus of claim 2, further comprising a closing tab on the lid configured to close off the nozzle.

4. The apparatus of claim 1, wherein the impeller comprises a double horse-shoe shape with a first horse shoe curved downward, and a second horse shoe curved upward so that the two are conjoined in a common plane at their respective apexes of curvature.

5. The apparatus of claim 1, wherein the baffle comprises a mesh material disposed in each perforation.

6. The apparatus of claim 1, wherein the housing and the container are sized to fit inside a cup-holder of a vehicle.

7. An apparatus for generating and distributing chlorine dioxide, the apparatus comprising:
    a container configured to contain water and a formulation that releases chlorine dioxide when in contact with water;
    a lid configured to attach to an upper open end of the container, the lid comprising a nozzle;
    an impeller positioned within the container;
    a base disposed at a bottom end of the container; and
    a motor coupled to the impeller and disposed in the base;
    wherein the impeller is configured to form a vortex within the water in the container, when rotated by the motor during use;
    wherein the lid and nozzle are configured to emit an air-borne spray comprising gaseous cleaning agent and entrained water droplets through the nozzle;
    wherein the lid includes a baffle configured to selectively allow passage of droplets of water based on droplet size, the baffle having a plurality of perforations.

8. The apparatus of claim 7, wherein the nozzle comprises a baffle, the baffle comprising through holes.

9. The apparatus of claim 8, further comprising a closing tab on the lid configured to close off the nozzle.

10. The apparatus of claim 7, wherein the impeller comprises a double horse-shoe shape with a first horse shoe curved downward, and a second horse shoe curved upward so that the two are conjoined in a common plane at their respective apexes of curvature.

11. The apparatus of claim 7, wherein the baffle comprises a mesh material.

12. The apparatus of claim 7, wherein the base and the container are sized to fit inside a cup-holder of a vehicle.

13. An apparatus for generating and distributing chlorine dioxide, the apparatus comprising:
    a container having a lid, the container configured to contain water and a formulation that releases chlorine dioxide when in contact with water, wherein the lid comprises a nozzle configured to emit an air-borne spray comprising chlorine dioxide and water, further wherein the lid comprises a baffle that is configured to selectively allow passage of droplets of water based on droplet size, the baffle having a plurality of perforations;
    an agitator positioned within the container; and
    a driver for the agitator, associated with the container, to facilitate agitation of water within the container, when the apparatus is in use;
    wherein the agitator is configured to promote the release of chlorine dioxide from a formulation comprising a tablet or gel pack.

14. The apparatus of claim 13, wherein the container is configured to generate and distribute sufficient chlorine dioxide gas to remove malodor from an automotive cabin interior within about 10 to about 20 minutes.

15. The apparatus of claim 13, wherein the container is configured to generate and distribute sufficient chlorine dioxide gas to reduce a contamination load by at least 80% when deployed in an automotive cabin.

16. The apparatus of claim 13, wherein the baffle comprises a mesh material.

17. The apparatus of claim 13, wherein the container is sized to fit inside a cup-holder of a vehicle.

* * * * *